United States Patent
Amo et al.

(10) Patent No.: US 8,628,869 B2
(45) Date of Patent: Jan. 14, 2014

(54) MAGNETIC MEDIA AND MAGNETIC RECORDING DEVICES USING FLUORINE COMPOUNDS

(75) Inventors: Mina Amo, Ibaraki (JP); Katsumi Mabuchi, Ibaraki (JP); Hiroshi Yoshida, Ibaraki (JP); Bruno Marchon, Palo Alto, CA (US); Qing Dai, San Jose, CA (US)

(73) Assignee: HGST Netherlands B.V., Amsterdam (NL)

( * ) Notice: Subject to any disclaimer, the term of this patent is extended or adjusted under 35 U.S.C. 154(b) by 184 days.

(21) Appl. No.: 13/361,896

(22) Filed: Jan. 30, 2012

(65) Prior Publication Data
US 2013/0194693 A1 Aug. 1, 2013

(51) Int. Cl.
*G11B 5/66* (2006.01)

(52) U.S. Cl.
USPC ...... 428/835.8; 508/582; 508/280; 548/264.6

(58) Field of Classification Search
None
See application file for complete search history.

(56) References Cited

U.S. PATENT DOCUMENTS

| | | | |
|---|---|---|---|
| 5,225,549 A | 7/1993 | Dekura | |
| 6,376,065 B1 | 4/2002 | Korba et al. | |
| 7,449,266 B2 | 11/2008 | Flynn et al. | |
| 7,459,415 B1 | 12/2008 | Liu et al. | |
| 7,659,231 B2 | 2/2010 | Tonelli et al. | |
| 2008/0114177 A1 | 5/2008 | Boardman et al. | |
| 2010/0118436 A1 | 5/2010 | Yan et al. | |
| 2010/0267597 A1 | 10/2010 | Shimura et al. | |
| 2010/0323223 A1 | 12/2010 | Mabuchi et al. | |

FOREIGN PATENT DOCUMENTS

| | | |
|---|---|---|
| JP | 63171422 A | 7/1988 |
| JP | 3012817 A | 1/1991 |
| JP | 2005120146 A | 5/2005 |
| JP | 2009/003998 | 1/2009 |
| WO | 2010/115855 A1 | 10/2010 |

OTHER PUBLICATIONS

Solvay Solexis Product Data Sheet, Fomblin Z, Dec. 2002.*

* cited by examiner

*Primary Examiner* — Holly Rickman
(74) *Attorney, Agent, or Firm* — Zilka-Kotab, PC

(57) ABSTRACT

According to one embodiment, a lubricant includes a perfluoropolyether having a chemical structure of:

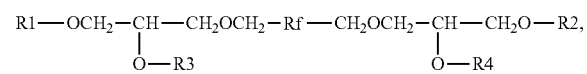

wherein Rf is at least one of: $-CF_2O(CF_2CF_2O)_m(CF_2O)_nCF_2-$ and $-CF_2CF_2O(CF_2CF_2CF_2O)_kCF_2CF_2-$, with m representing 0 or a positive integer, n representing 0 or a positive integer, and k representing 0 or a positive integer, and wherein R1 to R4 are selected from a group consisting of —H or

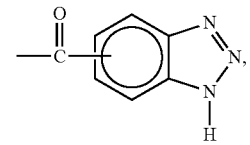

with at least one of R1 to R4 being

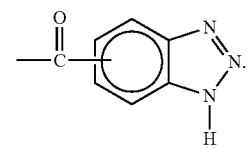

20 Claims, 7 Drawing Sheets

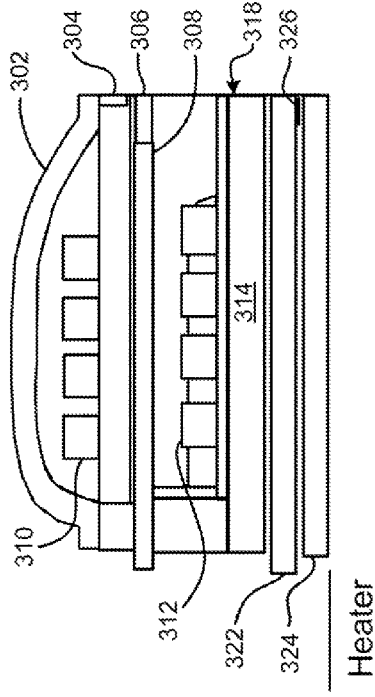
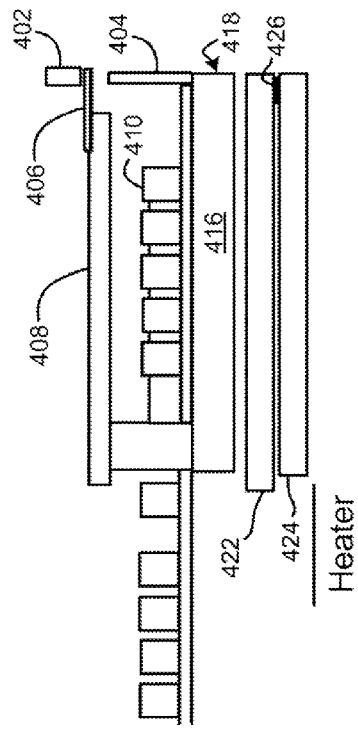
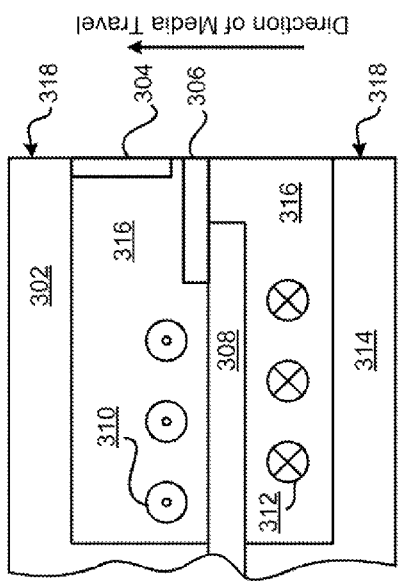
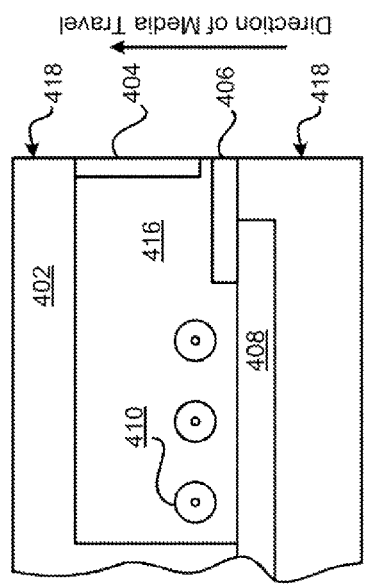

MAGNETIC MEDIA AND MAGNETIC RECORDING DEVICES USING FLUORINE COMPOUNDS

FIELD OF THE INVENTION

The present application relates to fluorine compounds, and particularly to magnetic recording devices and magnetic media using fluorine compounds.

BACKGROUND

Conventional magnetic recording and reading devices, such as hard disk drives, optical drives, etc., are optimized for many parameters to run at various temperatures and operating conditions. The allowable temperatures and conditions may be visualized as windows of operation where the conditions and temperatures allow for consistently superior performance. These windows of operation have been getting smaller and smaller due to difficulties associated with areal density, such as a super-paramagnetic limit, size constraints, tolerances, process control limitations, etc. Operation of magnetic devices at cold temperatures, as an example, often requires additional write-ability of a magnetic recording head, and at higher temperatures is capable of writing in a manner which limits the thermal instability of a magnetic recording medium. In addition, surplus write current which is used for higher write-ability usually induces large thermal protrusion of write poles, which is equivalent to lower thermal fly-height control (TFC) power, which often results in poor head-disk interface (HDI) reliability, even at low temperatures.

Some attempts have been made at correcting for these issues. In one scheme to improve the write-ability of a magnetic recording head, a localized AC field is applied at adequate frequency to the medium using a spin torque oscillator (STO). This scheme is referred to as microwave-assisted magnetic recording (MAMR). However, it is very difficult to generate a localized AC field at microwave frequencies in a stable and reliable enough manner to assist high density magnetic recording in a thermally stable medium using a STO. Because an injected current density necessary to generate an appropriate AC field at microwave frequencies to assist high density magnetic recording is too high, such as $10^8$-$10^9$ A/cm$^2$, stable and reliable operation is often prevented using this scheme due to electro-migration.

In order to improve upon the record density of magnetic media, discrete track media (DTM) and bit patterned media (BPM) have been developed. In DTM, adjacent recording tracks are separated by slots, grooves, or a non-magnetic material, such as alumina, which controls or causes the magnetic interference between the adjacent tracks to be reduced or eliminated. In BTM, adjacent recorded bits are separated by grooves or non-magnetic material and the magnetic interference between the adjacent bits is reduced or prevented. However, there are still problems with each of these recording schemes.

In DTM recording, concave-convex processing is given to a magnetic layer, such as by dry etching, etc. After that, the slot between adjacent tracks is filled with a non-magnetic material. During this processing, there is a possibility that read-write (RW) characteristics of the media may deteriorate quickly, such as from corrosion that is due to damage to the magnetic layer that is suffered at the time of the processing. Other factors may also lead to a deterioration of the RW characteristics of the magnetic media due to the processing. With conventional magnetic recording media where no patterning or discrete tracks are formed, corrosion inhibition is improved by using lubricants which include triazoles. Furthermore, the formation of lubricating films in which perfluoropolyether and corrosion inhibitors are used conjointly on patterned media and the formation of lubricating films in which heterocycles which have a corrosion inhibiting action are included in a perfluoropolyether have also been suggested.

In another attempt to improve upon the record density of magnetic media, thermal assisted recording (TAR) has been developed. In TAR, the magnetic recording media surface is locally heated above about 300° C., such as by laser light, in the presence of an applied magnetic field, which reduces the magnetic coercive force and makes it easier to magnetically record data. However, during this process there is a possibility that any lubricant on the surface may suffer from heat decomposition, and overall evaporation of the lubricant may be accelerated.

SUMMARY

According to one general embodiment, a lubricant includes a perfluoropolyether having a chemical structure of:

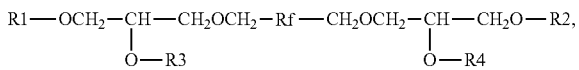

wherein Rf is at least one of: —CF$_2$O(CF$_2$CF$_2$O)$_m$(CF$_2$O)$_n$CF$_2$— and —CF$_2$CF$_2$O(CF$_2$CF$_2$CF$_2$O)$_k$CF$_2$CF$_2$—, with m representing 0 or a positive integer, n representing 0 or a positive integer, and k representing 0 or a positive integer, and wherein R1, R2, R3 and R4 are selected from a group consisting of —H or

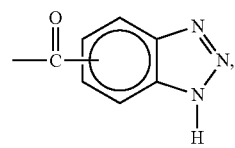

with at least one of R1, R2, R3 and R4 being

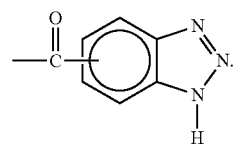

In another general embodiment, a lubricant includes a perfluoropolyether having a chemical structure of:

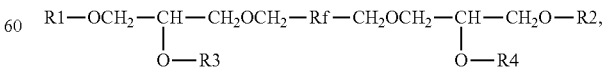

wherein Rf includes: —CF$_2$O(CF$_2$CF$_2$O)$_m$(CF$_2$O)$_n$CF$_2$—, with m representing 0 or a positive integer, n representing 0 or a positive integer, and wherein R1, R2, R3 and R4 are selected from a group consisting of —H or

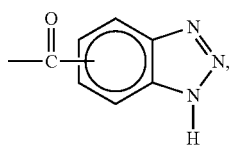

with at least one of R1, R2, R3 and R4 being

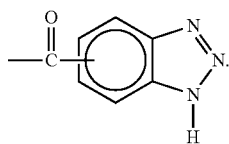

In another general embodiment, a lubricant includes a perfluoropolyether having a chemical structure of:

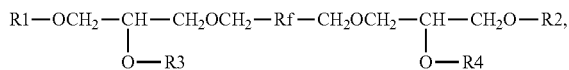

wherein Rf comprises: $-CF_2CF_2O(CF_2CF_2CF_2O)_kCF_2CF_2-$, with k representing 0 or a positive integer, wherein R1, R2, R3 and R4 are selected from a group consisting of —H or

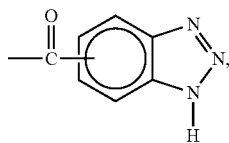

with at least one of R1 to R4 being

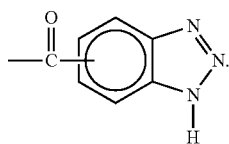

Any of these embodiments may be implemented in a magnetic data storage system such as a disk drive system, which may include a magnetic head, a drive mechanism for passing a magnetic storage medium (e.g., hard disk) over the head, and a control unit electrically coupled to the head for controlling operation of the head.

Other aspects and advantages of the present invention will become apparent from the following detailed description, which, when taken in conjunction with the drawings, illustrate by way of example the principles of the invention.

BRIEF DESCRIPTION OF THE DRAWINGS

FIG. 3A is a cross-sectional view of one particular embodiment of a perpendicular magnetic head with helical coils.

FIG. 3B is a cross-sectional view of one particular embodiment of a piggyback magnetic head with helical coils.

FIG. 4A is a cross-sectional view of one particular embodiment of a perpendicular magnetic head with looped coils.

FIG. 4B is a cross-sectional view of one particular embodiment of a piggyback magnetic head with looped coils.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an," and "the" include plural referents unless otherwise specified.

According to one general embodiment, a lubricant includes a perfluoropolyether having a chemical structure of:

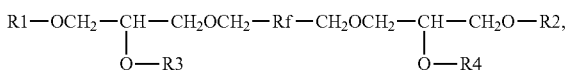

wherein Rf is at least one of: $-CF_2O(CF_2CF_2O)_m(CF_2O)_nCF_2-$ and $-CF_2CF_2O(CF_2CF_2CF_2O)_kCF_2CF_2-$, with m representing 0 or a positive integer, n representing 0 or a positive integer, and k representing 0 or a positive integer, and wherein R1 to R4 are selected from a group consisting of —H or with at least one of R1 to R4 being

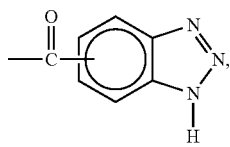

In another general embodiment, a lubricant includes a perfluoropolyether having a chemical structure of:

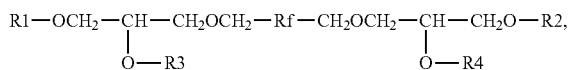

wherein Rf includes: $-CF_2O(CF_2CF_2O)_m(CF_2O)_nCF_2-$, with m representing 0 or a positive integer, n representing 0 or a positive integer, and wherein R1 to R4 are selected from a group consisting of —H or

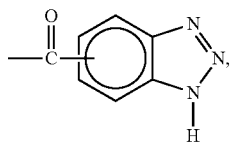

with at least one of R1 to R4 being

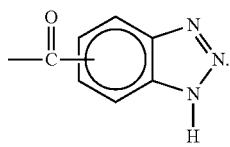

In another general embodiment, a lubricant includes a perfluoropolyether having a chemical structure of:

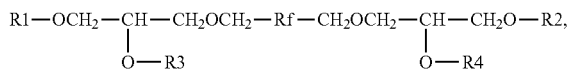

wherein Rf comprises: $-CF_2CF_2O(CF_2CF_2CF_2O)_kCF_2CF_2-$, with k representing 0 or a positive integer, wherein R1 to R4 are selected from a group consisting of —H or

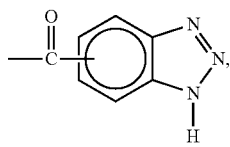

with at least one of R1 to R4 being

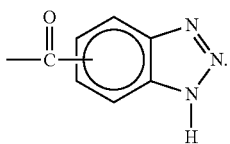

In data storage devices which combine recent recording technologies, e.g., discrete track media (DTM), bit patterned media (BPM), and thermal assisted recording (TAR), it will be important for a lubricant on any recording media surfaces to have a high heat resistance, to provide corrosion protection and have resistance to corrosion, and to suffer from neither heat decomposition nor evaporation in conditions of partial heating of 300° C. or more. In order to overcome this problem, a lubricant which includes corrosion protection and provides corrosion protection to magnetic media to which it is applied along with a high heat resistance may be used in DTM, BPM, and TAR recording systems, according to one embodiment.

Figure 1:
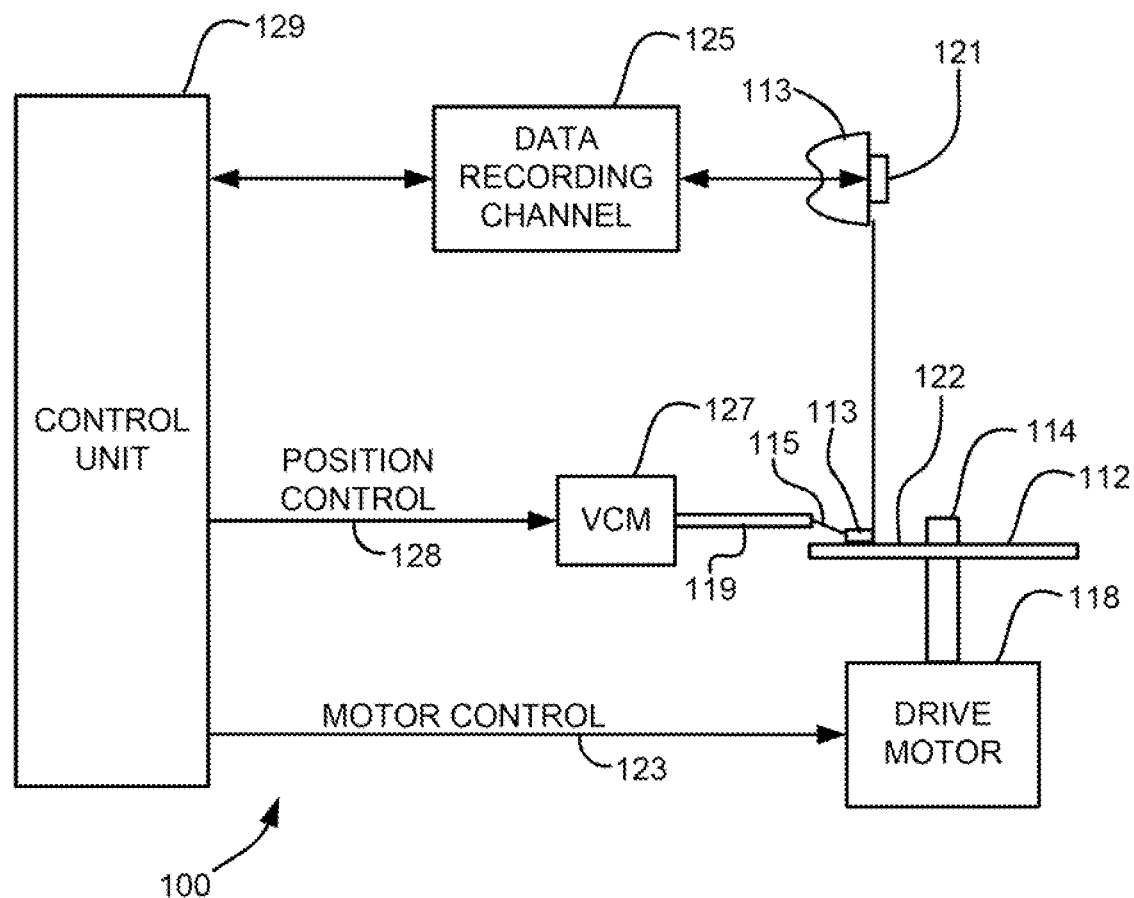
FIG. 1 is a simplified drawing of a magnetic recording disk drive system.

Referring now to FIG. 1, there is shown a disk drive 100 in accordance with one embodiment of the present invention. As shown in FIG. 1, at least one rotatable magnetic disk 112 is supported on a spindle 114 and rotated by a disk drive motor 118. The magnetic recording on each disk is typically in the form of an annular pattern of concentric data tracks (not shown) on the disk 112.

At least one slider 113 is positioned near the disk 112, each slider 113 supporting one or more magnetic read/write heads 121. As the disk rotates, slider 113 is moved radially in and out over disk surface 122 so that heads 121 may access different tracks of the disk where desired data are recorded and/or to be written. Each slider 113 is attached to an actuator arm 119 by means of a suspension 115. The suspension 115 provides a slight spring force which biases slider 113 against the disk surface 122. Each actuator arm 119 is attached to an actuator 127. The actuator 127 as shown in FIG. 1 may be a voice coil motor (VCM). The VCM comprises a coil movable within a fixed magnetic field, the direction and speed of the coil movements being controlled by the motor current signals supplied by controller 129.

During operation of the disk storage system, the rotation of disk 112 generates an air bearing between slider 113 and disk surface 122 which exerts an upward force or lift on the slider. The air bearing thus counter-balances the slight spring force of suspension 115 and supports slider 113 off and slightly above the disk surface by a small, substantially constant spacing during normal operation. Note that in some embodiments, the slider 113 may slide along the disk surface 122.

The various components of the disk storage system are controlled in operation by control signals generated, by control unit 129, such as access control signals and internal clock signals. Typically, control unit 129 comprises logic control circuits, storage (e.g., memory), and a microprocessor. The control unit 129 generates control signals to control various system operations such as drive motor control signals on line 123 and head position and seek control signals on line 128. The control signals on line 128 provide the desired current profiles to optimally move and position slider 113 to the desired data track on disk 112. Read and write signals are communicated to and from read/write heads 121 by way of recording channel 125.

The above description of a typical magnetic disk storage system, and the accompanying illustration of FIG. 1 is for representation purposes only. It should be apparent that disk storage systems may contain a large number of disks and actuators, and each actuator may support a number of sliders.

An interface may also be provided for communication between the disk drive and a host (integral or external) to send and receive the data and for controlling the operation of the disk drive and communicating the status of the disk drive to the host, all as will be understood by those of skill in the art.

In a typical head, an inductive write head includes a coil layer embedded in one or more insulation layers (insulation stack), the insulation stack being located between first and second pole piece layers. A gap is formed between the first and second pole piece layers by a gap layer at an air bearing surface (ABS) of the write head. The pole piece layers may be connected at a back gap. Currents are conducted through the coil layer, which produce magnetic fields in the pole pieces. The magnetic fields fringe across the gap at the ABS for the purpose of writing bits of magnetic field information in tracks on moving media, such as in circular tracks on a rotating magnetic disk.

The second pole piece layer has a pole tip portion which extends from the ABS to a flare point and a yoke portion which extends from the flare point to the back gap. The flare point is where the second pole piece begins to widen (flare) to form the yoke. The placement of the flare point directly affects the magnitude of the magnetic field produced to write information on the recording medium.

According to one illustrative embodiment, a magnetic data storage system may comprise at least one magnetic head as described herein according to any embodiment, a magnetic medium, a drive mechanism for passing the magnetic medium over the at least one magnetic head, and a controller electrically coupled to the at least one magnetic head for controlling operation of the at least one magnetic head.

Figure 2E:
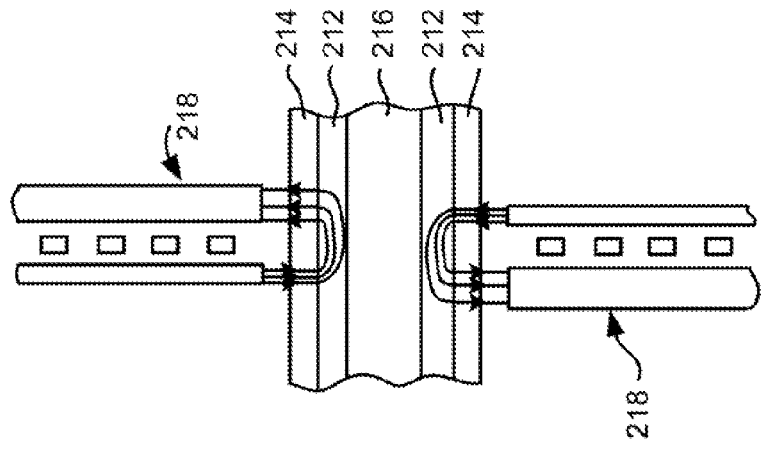
FIG. 2E is a schematic representation of a recording apparatus adapted for recording separately on both sides of the medium.
Figure 2C:
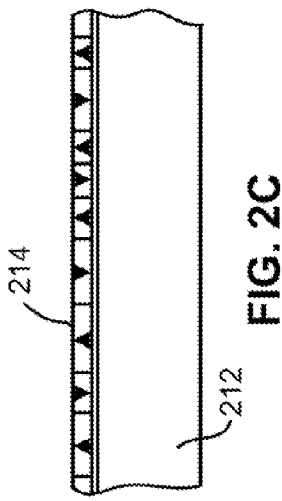
FIG. 2C is a magnetic recording medium utilizing a perpendicular recording format.
Figure 2D:
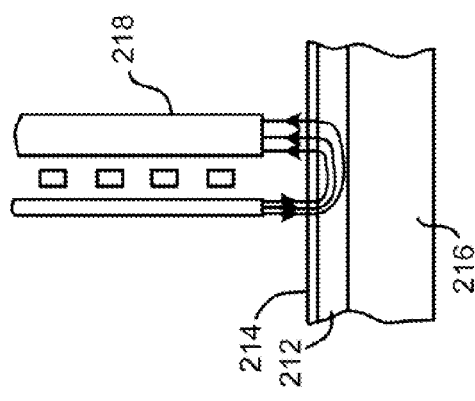
FIG. 2D is a schematic representation of a recording head and recording medium combination for perpendicular recording on one side.
Figure 2A:
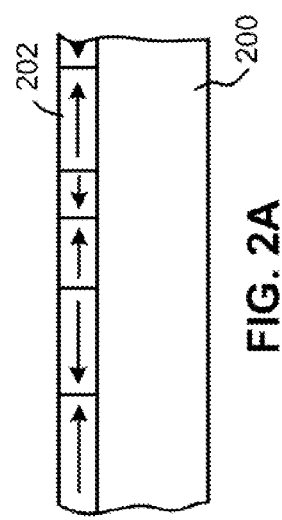
FIG. 2A is a schematic representation in section of a recording medium utilizing a longitudinal recording format.

FIG. 2A illustrates, schematically, a conventional recording medium such as used with magnetic disc recording systems, such as that shown in FIG. 1. This medium is utilized for recording magnetic impulses in or parallel to the plane of the medium itself. The recording medium, a recording disc in this instance, comprises basically a supporting substrate 200 of a suitable non-magnetic material such as glass, with an overlying coating 202 of a suitable and conventional magnetic layer.

Figure 2B:
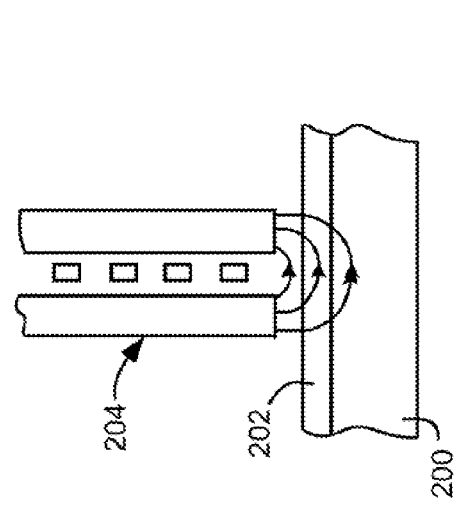
FIG. 2B is a schematic representation of a conventional magnetic recording head and recording medium combination for longitudinal recording as in FIG. 2A.

FIG. 2B shows the operative relationship between a conventional recording/playback head 204, which may preferably be a thin film head, and a conventional recording medium, such as that of FIG. 2A.

FIG. 2C illustrates, schematically, the orientation of magnetic impulses substantially perpendicular to the surface of a recording medium as used with magnetic disc recording systems, such as that shown in FIG. 1. For such perpendicular recording the medium typically includes an under layer 212 of a material having a high magnetic permeability. This under layer 212 is then provided with an overlying coating 214 of magnetic material preferably having a high coercivity relative to the under layer 212.

FIG. 2D illustrates the operative relationship between a perpendicular head 218 and a recording medium. The recording medium illustrated in FIG. 2D includes both the high permeability under layer 212 and the overlying coating 214 of magnetic material described with respect to FIG. 2C above. However, both of these layers 212 and 214 are shown applied to a suitable substrate 216. Typically there is also an additional layer (not shown) called an "exchange-break" layer or "interlayer" between layers 212 and 214.

In this structure, the magnetic lines of flux extending between the poles of the perpendicular head 218 loop into and out of the overlying coating 214 of the recording medium with the high permeability under layer 212 of the recording medium causing the lines of flux to pass through the overlying coating 214 in a direction generally perpendicular to the surface of the medium to record information in the overlying coating 214 of magnetic material preferably having a high coercivity relative to the under layer 212 in the form of magnetic impulses having their axes of magnetization substantially perpendicular to the surface of the medium. The flux is channeled by the soft underlying coating 212 back to the return layer (P1) of the head 218.

FIG. 2E illustrates a similar structure in which the substrate 216 carries the layers 212 and 214 on each of its two opposed sides, with suitable recording heads 218 positioned adjacent the outer surface of the magnetic coating 214 on each side of the medium, allowing for recording on each side of the medium.

FIG. 3A is a cross-sectional view of a perpendicular magnetic head. In FIG. 3A, helical coils 310 and 312 are used to create magnetic flux in the stitch pole 308, which then delivers that flux to the main pole 306. Coils 310 indicate coils extending out from the page, while coils 312 indicate coils extending into the page. Stitch pole 308 may be recessed from the ABS 318. Insulation 316 surrounds the coils and may provide support for some of the elements. The direction of the media travel, as indicated by the arrow to the right of the structure, moves the media past the lower return pole 314 first, then past the stitch pole 308, main pole 306, trailing shield 304 which may be connected to the wrap around shield (not shown), and finally past the upper return pole 302. Each of these components may have a portion in contact with the ABS 318. The ABS 318 is indicated across the right side of the structure.

Perpendicular writing is achieved by forcing flux through the stitch pole 308 into the main pole 306 and then to the surface of the disk positioned towards the ABS 318.

FIG. 3B illustrates a piggyback magnetic head having similar features to the head of FIG. 3A. Two shields 304, 314 flank the stitch pole 308 and main pole 306. Also sensor shields 322, 324 are shown. The sensor 326 is typically positioned between the sensor shields 322, 324.

FIG. 4A is a schematic diagram of one embodiment which uses looped coils 410, sometimes referred to as a pancake configuration, to provide flux to the stitch pole 408. The stitch pole then provides this flux to the main pole 406. In this orientation, the lower return pole is optional. Insulation 416 surrounds the coils 410, and may provide support for the stitch pole 408 and main pole 406. The stitch pole may be recessed from the ABS 418. The direction of the media travel, as indicated by the arrow to the right of the structure, moves the media past the stitch pole 408, main pole 406, trailing shield 404 which may be connected to the wrap around shield (not shown), and finally past the upper return pole 402 (all of which may or may not have a portion in contact with the ABS 418). The ABS 418 is indicated across the right side of the structure. The trailing shield 404 may be in contact with the main pole 406 in some embodiments.

FIG. 4B illustrates another type of piggyback magnetic head having similar features to the head of FIG. 4A including a looped coil 410, which wraps around to form a pancake coil. Also, sensor shields 422, 424 are shown. The sensor 426 is typically positioned between the sensor shields 422, 424.

In FIGS. 3B and 4B, an optional heater is shown near the non-ABS side of the magnetic head. A heater element (Heater) may also be included in the magnetic heads shown in FIGS. 3A and 4A. The position of this heater may vary based on design parameters such as where the protrusion is desired, coefficients of thermal expansion of the surrounding layers, etc.

In order to realize a high level of corrosion resistance in respect of the corrosion of metals or metal alloys which form the magnetic film, etc., and to have a high level of heat resistance and a firm attachment so that thermal degradation and vaporization are unlikely to occur due to local heating to 300° C. or above, certain embodiments and approaches are described below.

In one embodiment, corrosion inhibitors, which are fluorine-free compounds typically, are added to a perfluoropolyether, which is a fluorine-based lubricant, to form a lubricant that has superior corrosion resistance. Generally, when fluorine-based compounds and fluorine-free compounds, are mixed together, they are incompatible and phase separation occurs. Therefore, it is typically difficult to form a uniform film, and there is a risk that the corrosion inhibiting effect of the formed film will be reduced.

For example, even if it is temporarily dissolved, the fluorine-free compound precipitates out as time passes and the lubricating film is liable to make contact with the recording head and, depending on the particular case, the precipitated material may become attached to the head surface and the stability of the head flotation may not be maintained. Lubricants into which triazoles have been introduced via the terminal ester groups (—COO—) of the lubricant are susceptible to hydrolysis since ester groups (—COO—) are being used, the triazoles are released, and terminal carboxylic acid groups (—COOH) are formed and a corrosion inhibiting effect is not obtained. Moreover, in the prior art, a high level of attachment and heat resistance characteristics in respect of local heating to 300° C. or above have not been materialized and the countermeasures against such heating are not satisfactory.

As a result of thorough experiments carried out in an attempt to raise corrosion resistance and heat resistance of lubricant films, as well as the level of fixation on the magnetic recording medium surface of perfluoropolyether-based lubricating films, it has been discovered that the abovementioned problems may be resolved by introducing specified functional groups as terminal groups on the perfluoropolyether. That is to say, the use of perfluoropolyethers which have a certain chemical structure as one or more terminal groups, and not carboxyl groups, starting with ester groups and ether groups for example, which have not been used conventionally as lubricants, greatly improves the heat resistance and the corrosion inhibiting effect in respect of corrosion of the metals and metal alloys from which the magnetic film, etc., is formed. One of the chemical structures which may be used includes at least one

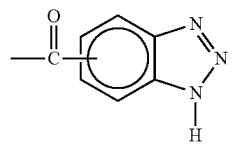

group (referred to herein as Group I) and any hydrogen groups (—H).

Moreover, it has been discovered that the number of Group I introduced onto the ends of the perfluoropolyether also contributes greatly toward adhesion of the lubricating film to the metal alloys, magnetic films, etc., to which it is to be attached, according to one embodiment.

In one embodiment, a lubricant, which may be formed above a magnetic recording layer of a magnetic medium, may be characterized by having a benzotriazole (BTA) group at an end with a perfluoropolyether structure according to the chemical structure as shown below.

(Chemical Structure I)

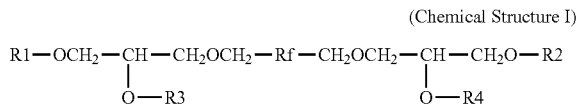

In Chemical Structure I, Rf is at least one of: —CF$_2$O (CF$_2$CF$_2$O)$_m$(CF$_2$O)$_n$CF$_2$— and/or —CF$_2$CF$_2$O(CF$_2$CF$_2$CF$_2$O)$_k$CF$_2$CF$_2$—, with m representing 0 or a positive integer, n representing 0 or a positive integer, and k representing 0 or a positive integer, wherein R1 to R4 are selected from a group consisting of —H or

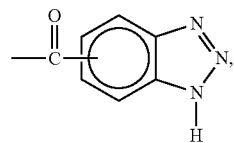

with at least one of R1 to R4 being

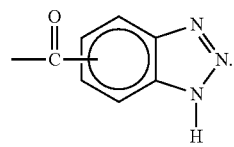

Any positive integer may be used as m, n, or k, such as 1, 2, 5, 10, 25, 50, 100, etc.

According to various embodiments, the fluoride-including compound of Chemical Structure I is excellent in corrosive protection resistance and heat resistance to the corrosion of cobalt. By using a lubricant including Chemical Structure I, and applying the lubricant to an upper surface of a magnetic recording medium, it becomes possible to incorporate the outstanding recording reproduction capability and outstanding dirt-proof, wear-proof, and long-term run stability afforded due to this lubricant layer.

According to one embodiment, the lubricant may be characterized in that the degree of difunctional content of Group I in the lubricant is at least 25%. Moreover, the degree of difunctional content signifies the proportion of terminal groups represented by Group I with respect to all of the terminal groups of the perfluoropolyether of Structure I. For example, when R1 and R2, which are both terminal groups of Rf, are Group I, the degree of difunctional content is 50%. The degree of difunctional content is obtained by measuring the $^1$H chemical shifts using Fourier transform type nuclear magnetic resonance (FT-NMR) and is calculated from the area ratio of —CH$_2$— and —CH— in the terminal functional groups of the perfluoropolyether and the area ratio of H in the benzene rings of the BTA.

If the degree of substitution is about 25% or more, then the lubricant has corrosion inhibiting properties in respect to cobalt, iron, and alloys thereof, which may be used in the magnetic layer. Furthermore, if the lubricant has heat resistance in respect of local heating to 300° C. or above, then it is possible to keep corrosion of the magnetic recording medium and thermal degradation and vaporization of the lubricating film low. Furthermore, there are also terminal hydroxyl groups (where R1 to R4 represent —H) on the perfluoropolyether and so the adhesion on the magnetic recording medium may also be maintained with these hydroxyl groups.

According to one embodiment, the degree of difunctional content of the lubricant is at least about 25%, and more desirably in a range from about 40% to about 80%. Furthermore, the lubricant, in some approaches, may be characterized in that an average molecular weight (Mn) of the lubricant may be from about 1,500 to about 4,500. In addition, in one embodiment, a molecular weight distribution of the lubricant may be about 1.5 or less, and in a more preferred embodiment, it may be from about 1.0 to about 1.2.

The Mn of the lubricant was calculated using $^{19}$F-FT-NMR. Furthermore, measurement of the molecular weight distribution (Mw/Mn) was carried out using gel permeation chromatography (GPC). GPC analysis was carried out with high performance liquid chromatography (HPLC).

The lubricants described herein according to various embodiments, for example the perfluoropolyethers which have organic terminal groups R1 to R4 which can be represented by Chemical Structure I, may be produced by methods in which perfluoropolyethers which have terminal hydroxyl groups (where R1 to R4 are all —H) are subjected to a water-eliminating condensation reaction in the presence of an acid catalyst with substances which have specified organic groups which become terminal groups comprising Group I. When a perfluoropolyether is used as a lubricant, it may be dissolved in a solvent, additives, surfactants and the like can be added, as desired by one of skill in the art, and coated on a magnetic recording medium, in one approach.

No particular limitation is imposed upon the method of coating, but use of the dip-coating method or spin-coating method may be used. The chosen solvent is one in which the perfluoropolyether dissolves. In practical terms, examples of solvents which may be used include FC-72, FC-75, FC-77, PF-5080, PF-5052, and the FIFE series produced by the 3M CO., VERTREL XF, XE, and XM produced by the DUPONT CO. and AK225 produced by the ASAHI GLASS CO. Furthermore, mixtures of fluorinated solvents and fluorine-free solvents may also be used in other embodiments.

The concentration of the coating solution differs according to the type of lubricant and the type of solvent, but in one embodiment, a concentration in solution of from about 0.1 to 5 g/l may be used. The adhesion of the lubricant on the substrate may be due to heat treatment, irradiation with light having a wavelength of 254 nm, 185 nm, 172 nm, or the like, or by carrying out both of these treatments after forming the lubricating layer.

In terms of the lubricating layer thickness, a thin layer is preferred so that there is no contact with the head since it is included within the floating range of the head, in one embodiment. For example, a thickness within a range from about 0.5 nm to about 2.0 nm may be used in one approach. The lubricating film thickness was measured with Fourier transform type infrared spectrophotometer (FT-IR).

Next the construction of the magnetic recording medium using the perfluoropolyethers described herein according to various embodiments is described.

In one embodiment, magnetic discs may comprise a laminated structure where at least a magnetic recording layer and a protective film have been formed on a nonmagnetic substrate, and then a lubricating film according to any embodiments and/or approaches described herein is formed on the surface of the protective film. The protective film is optional, as it is not a requirement for the magnetic medium to include a protective film, or the protective film may be a part of the magnetic recording layer, according to various embodiments.

In another embodiment, the magnetic medium may be a bit patterned medium (BPM), a discrete track medium (DTM), or some other type of patterned media as would be understood by one of skill in the art.

Figure 5:
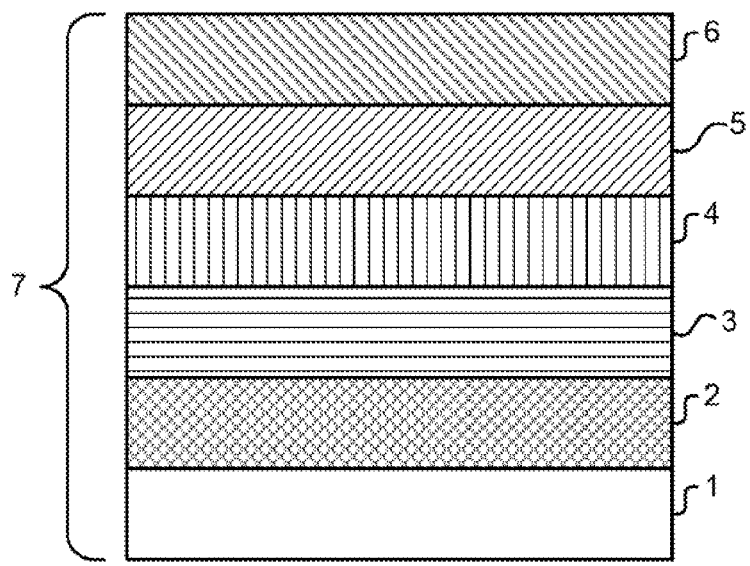
FIG. 5 is a cross-sectional schematic diagram of a magnetic disc, according to one embodiment.

A cross-sectional schematic diagram of a magnetic disc is shown in FIG. 5, according to one embodiment. This magnetic disc 7 is constructed with a laminated structure where the seed film 2, the undercoat film 3, the recording layer 4 comprising at least one layer, the protective film 5 and the lubricating film 6 have been formed sequentially on the substrate 1. Here, in cases where the head load is small, the protective layer may be omitted provided that a recording layer of a certain strength is ensured or damage to the magnetic recording layer is not anticipated. The substrate may be, for example, an aluminum alloy, a ceramic such as glass, a polycarbonate, or any other material as would be known by one of skill in the art. The substrate may have any thickness, and may be formed using any technique known in the art. The seed film 2 may be formed with a NiTa alloy or any other material as would be known by one of skill in the art. The undercoat film 3 may be formed with a Ni—P alloy, a Ni—Al alloy, or any other material as would be known by one of skill in the art. The structural material of the magnetic layers which form the recording layer 4 of the magnetic disc 7 may include elements which can form ferromagnetic bodies such as iron, cobalt, nickel, or any other material as would be known by one of skill in the art. These materials include alloys where chromium, platinum, tantalum, or any other material as would be known by one of skill in the art, have been added to these metals, and/or their oxides. These may be formed with a plating method or with a sputtering method, or any other method as would be known by one of skill in the art. A hard carbon film, such as a diamond-like carbon (DLC) film or the like may be used, for example, for the protective layer 5, but there also cases where SiC, SiO, or any other material as would be known by one of skill in the art may be used. These layers may be formed using a sputtering method, or any other method as would be known by one of skill in the art.

Furthermore, in those cases where the protective layer is formed with a sputtering method, a hardness of the protective layer may be raised by carrying out the sputtering under an Ar/N$_2$ gas atmosphere. The lubricating film 6 may be formed from any lubricant described herein. The construction of a magnetic disc using this approach and the structural materials other than the lubricating film described herein are well known and so they are not described in detail here.

Figure 6:
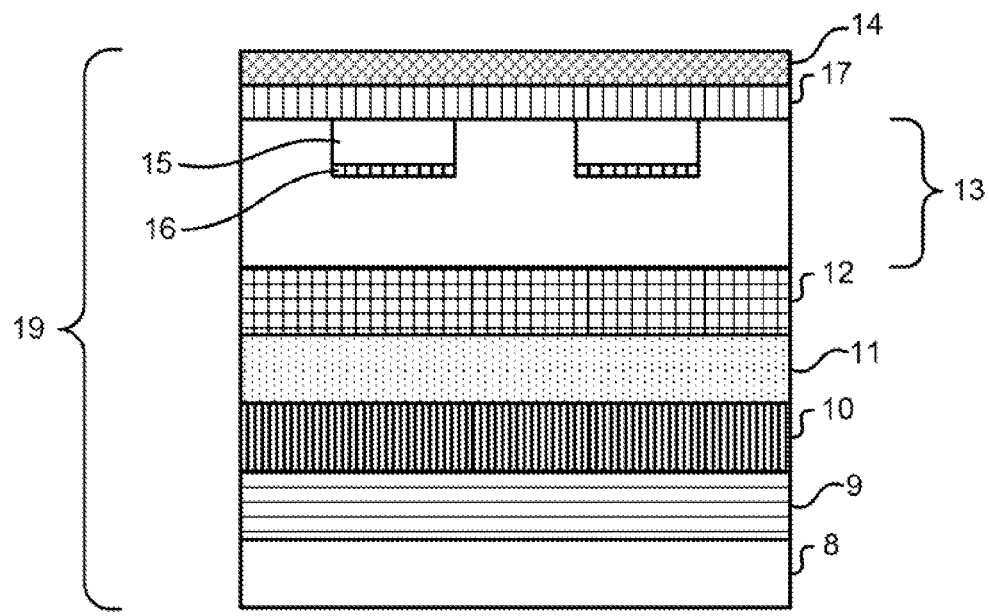
FIG. 6 is a cross-sectional schematic diagram of patterned medium, according to one embodiment.

A cross-sectional schematic diagram of patterned medium is shown in FIG. 6, according to one embodiment. This magnetic disc 19 has a binding layer 9, a soft magnetic undercoat layer 10, a seed layer 11, an intermediate layer 12, and a recording layer 13 formed on a substrate 8. The substrate may comprise glass or any other suitable material as would be known to one of skill in the art. Concavities and protrusions are formed in the recording layer 13 and the protruding parts form magnetic regions 14 while the concave parts form the filled regions 15 (nonmagnetic parts). The protective film 17 is positioned above the recording layer and the lubricating film 18 is positioned above the protective film. Once again, the protective film 17 is not required. No particular limitation is imposed upon the material of the binding layer provided that it has excellent adhesion with the substrate and good planar surface flatness, but it may be preferably constructed with an alloy which includes at least two or more metals from among a list comprising: Ni, Al, Ti, Ta, Cr, Zr, Co, Hf, Si, and B. In more practical terms NiTa, AlTi, AlTa, CrTi, CoTi, NiTaZr, NiCrZr, NiCrAl, CrTiTa, CoTiNi, CoTiAl, or any other suitable material may be used as would be known to one of skill in the art.

No particular limitation is imposed upon the material of the soft magnetic undercoat layer provided that it has a saturation magnetic flux density (Bs) of at least about 1 tesla, imparts uniaxial anisotropy in the radial direction of the disc substrate, has a coercive force measured in the head running direction of not more than about 1.6 kA/m and excellent surface flatness. In more practical terms, the abovementioned characteristics may be obtained by using an amorphous alloy which has Co, Ni, or Fe as a main component to which Ta, Hf, Nb, Zr, Si, B, C, and/or other suitable materials have been added. Moreover, it is possible to reduce noise by making a laminated structure by introducing a nonmagnetic layer into the soft magnetic undercoat layer. Any material may be used as this nonmagnetic layer, such as CoCr alloys, Ru, Cr, Cu, MgO and/or other suitable materials as would be known to one of skill in the art.

The role of the seed layer is to control the orientation and crystal grain diameter of the intermediate layer, and face centered cubic (fcc) alloys which have Ni as a main component may be used in some approaches. Typically alloys where one or more metal selected from among W, Fe, Ta, Ti, Nb, Cr, Mo, V, Cu, etc., in an alloy with Ni may be used, according to various approaches. Furthermore, in order to improve the corrosion resistance, the seed layer may have a double-layer construction with the abovementioned seed layer as a seed layer on the recording layer side (second seed layer) with an alloy where Ta, Ti, Nb, Al, etc., has been added to Cr inserted as a first seed layer between the second seed layer and the soft magnetic layer, in another approach. Ru alone, or an alloy with a hexagonal close packed (hcp) lattice structure or fcc structure which has Ru as a main component may be used for the intermediate layer in various approaches.

An alloy which has a granular structure and includes a CoCr-based alloy, such as a CoCrPt alloy or the like or a FePt-based alloy or the like as a main component to which an oxide such as $SiO_2$ or the like has been added, such as CoCrPt—$SiO_2$, CoCrPtMgO, CoCrPt—TaO and the like, may be used as the magnetic layer material which forms the protruding parts of the recording layer. Furthermore, an oxide such as $SiO_2$, $Al_2O_3$, $TiO_2$, ferrite or the like, a nitride such as AlN or the like, a carbide such as SiC or the like, or any other suitable material as would be known by one of skill in the art may be used for the filling (non-magnetic) material which is formed in the concavities. For the concentrations of Co and Pt, a Cr concentration in a range from about 15 at % to about 25 at % and a Cr concentration in a range from about 10 at % to about 20 at % may be used in some approaches.

The protective film 16 which may be formed as the bottom part of the filling is a layer which is introduced in order to repair defects due to damage caused during magnetic layer processing and it is constructed with a layer of metal or alloy which has been rendered as a passive layer or a carbon layer. Cr, Ti, Ni, Mo, Nb, W, Ta, Zr, or an alloy which includes at least one of these metals may be used for the metal which has been rendered passive, in one embodiment. Alloys which contain Cr are especially desirable. A hard carbon film, as typified by DLC or the like may be used for the material of the protective film 17 which is formed above the recording layer. A lubricating film which is formed from a lubricant as described herein, may be positioned over the protective film.

Figure 7:
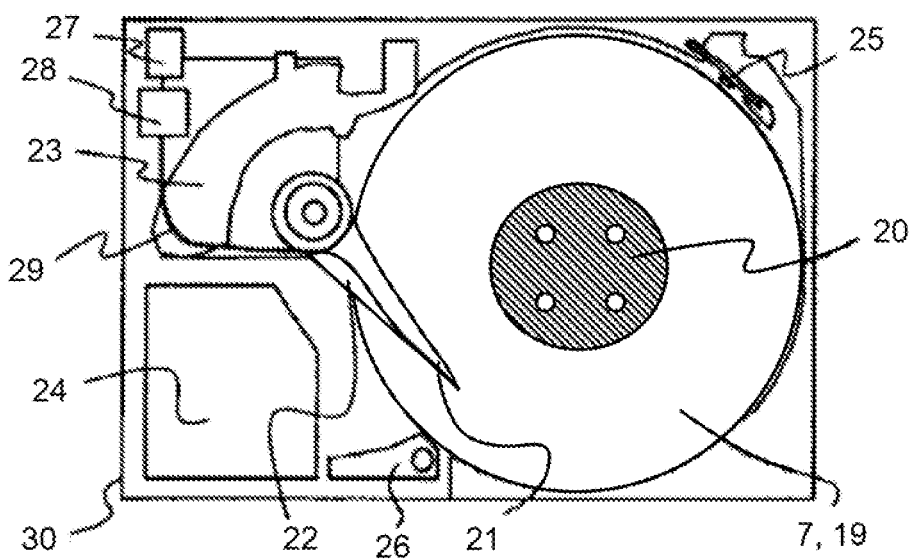
FIG. 7 is a plan schematic diagram of a magnetic disc apparatus, according to one embodiment.

The construction of the magnetic recording apparatus according to various embodiments will now be described. A plan schematic diagram of a magnetic disc apparatus is shown in FIG. 7, according to one embodiment. The magnetic disc apparatus described herein according to various embodiments is of the load/unload type and is constructed from a spindle 20 which rotates the magnetic disc, an arm 22 which supports the magnetic head 21, a voice coil motor 23 which positions the arm, a control circuit 24 which processes the signal, a dust filter 25 and a ramp 26 on which the head reposes during unload, etc. The magnetic head 21 may be a recording/play-back head which is furnished with a heating device which heats using close proximity light, and the laser light which is radiated from the semiconductor laser 27 which is the light source passes through the light switching device 28, is introduced into the magnetic head 21 through the optical fiber 29 and produces close proximity light. A thermal assist effect is obtained by the close proximity light which has been generated by heating the magnetic disc 30. It is possible to fix the memory capacity of the apparatus according to the number of magnetic discs loaded, the extent of head flotation, the magnetic characteristics of the magnetic layer, the head performance, etc.

According to one embodiment, the magnetic discs 7 and 19, which may have different magnetic disc constructions as described previously, such as a patterned medium and a non-patterned medium, for example, may be mounted in the magnetic disc apparatus. No particular limitation is imposed upon the method of operating the magnetic disc apparatus and a contact start/stop (CSS) system may be used.

It is possible to obtain lubricants which provide a high corrosion resistance and which have a high heat resistance while also being firmly attached and, by using these lubricants as lubricating films, magnetic recording media and magnetic recording apparatus which have excellent corrosion resistance, heat resistance, recording and play-back performance and long term running stability may be obtained.

Methods of synthesizing compounds 1 to 6 which are used in the illustrative examples are described below. Furthermore, the degrees of difunctional content of these compounds, and the average molecular weight (Mn) and molecular weight distributions (Mw/Mn) of the perfluoropolyethers as previously described which adhere to Chemical Structure I, are shown in Table 1.

TABLE 1

| Compound | Degree of Sub. (%) | Average Molecular Weight (Mn) | Molecular Weight Distribution (Mw/Mn) |
|---|---|---|---|
| Compound 1 | 66 | 1595 | 1.08 |
| Compound 2 | 98 | 1495 | 1.10 |
| Compound 3 | 48 | 1880 | 1.06 |
| Compound 4 | 15 | 1750 | 1.06 |
| Compound 5 | 58 | 1940 | 1.07 |
| Compound 6 | 78 | 1920 | 1.09 |

Compound 1 was formed of carboxytriazole (3.91 g, 24 mmol), 4-dimethylaminopyridine (0.32 g, 2.6 mmol), dimethylformamide (58 g) and a tert-butyl methyl ether (46 g) solution of ZTETRAOL 2000s produced by the SOLVAY SOLEXIS company (Mn of 1730 for Rf(F)=—$CF_2O$ $(CF_2CF_2O)_m(CF_2O)_nCF_2$—) (13.26 g, 6.0 mmol) which had four terminal hydroxyl groups, as a perfluoropolyether were added sequentially to a three-necked flask which had been fitted with a nitrogen bubbling tube and a stirrer. 1-Ethyl-3-(3-dimethylaminopropyl)carboxylmide hydrochloride (4.60 g, 24 mmol) was added at room temperature and stirred for 24 hours at 50° C. Water (60 g) and methyl isobutyl ketone (60 g) were added to the reaction solution and the liquid was partitioned. The organic layer was washed two or three times with 1% hydrochloric acid aqueous solution (50 g) and saturated salt water (50 g) and then dried with anhydrous sodium sulphate and concentrated and Compound 1 (10.1 g) was obtained. It was confirmed from the area ratio of ZTETRAOL 2000s terminal protons and carboxytriazole protons obtained by $^1$H-NMR that the degree of difunctional content of Compound 1 was 66%.

Furthermore, according to $^{19}$F-NMR, the average molecular weight (Mn) of the main chain Rf(F) of Compound 1 was 1595 and the molecular weight distribution (Mw/Mn) according to GPC Was 1.08.

Compound 2 (11.62 g) was synthesized using a similar method as for Compound 1 except that the molar ratio and amounts of the raw materials ZTETRAOL 2000s and carboxytriazole introduced were changed. The degree of difunctional content of the Compound 2 obtained was 98%, Mn was 1495 and Mw/Mn was 1.10.

Compound 3 was formed using carboxytriazole (4.59 g, 28.1 mmol), 4-dimethylaminopyridine (0.34 g, 2.8 mmol), dimethylformamide (67 g) and a tert-butyl methyl ether (52 g) solution of D-4OH produced by MORESCO company (Mn of 2055 for Rf(D)=—$CF_2CF_2O(CF_2CF_2CF_2O)_mCF_2CF_2$—) (14.44 g, 7.0 mmol) which had four terminal hydroxyl groups, as a perfluoropolyether were added sequentially to a three-necked flask which had been fitted with a nitrogen bubbling tube and a stirrer. 1-Ethyl-3-(3-dimethylaminopropyl)carboxylmide hydrochloride (5.39 g, 28.1 mmol) was added at room temperature and stirred for 15 hours. Water (70 g) and methyl isobutyl ketone (70 g) were added to the reaction solution and the liquid organic layer was washed two or three times with 1% hydrochloric acid aqueous solution (50 g) and saturated salt water (50 g) and then dried with anhydrous sodium sulphate and concentrated and Compound 3 (8.5 g) was obtained. It was confirmed from the are ratio of D-4OH terminal protons and carboxytriazole protons obtained by $^1$H-NMR that the degree of sparation of Compound 3 was 48%. Furthermore, according to $^{19}$F-NMR, the average molecular weight (Mn) of the main chain Rf(D) of Compound 3 was 1880 and the molecular weight distribution (Mw/Mn) according to GPC was 1.06.

Compound 4 (9.5 g) was synthesized using a similar method as for Compound 3 using similar raw materials as used for Compound 3 except that the reaction time was changed to 3.5 hours. The degree of difunctional content of Compound 4 obtained was 15%, Mn was 1750 and Mw/Mn was 1.06.

Compound 5 (8.0 g) was synthesized using a similar method as for Compound 3 using similar raw materials as used for Compound 3 except that the reaction time was changed to 23 hours. The degree of difunctional content of Compound 5 was 58%, Mn was 1940, and Mw/Mn was 1.07.

Compound 6 (13.5 g) was synthesized using a similar method as for Compound 3 using similar raw materials as used for Compound 3 except that the reaction was carried out for 62 hours at room temperature and 24 hours at 50° C. The degree of difunctional content of Compound 6 was 78%, Mn was 1920, and Mw/Mn was 1.09.

Figure 8:
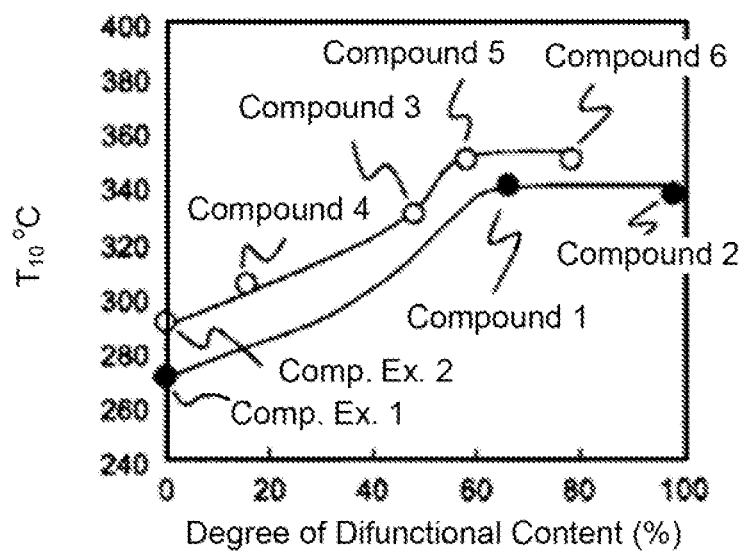
FIG. 8 is a chart depicting a relationship between degree of difunctional content and $T_{10}$ of the compounds tested, according to one embodiment.

Heat resistance tests were carried out with each compound using thermogravimetric analysis in order to investigate the heat resistance of the compounds (a total of six types) which were obtained. For the measurements, the temperature was raised at a rate of 5° C./minute under a nitrogen atmosphere and the temperature at which there was a 10% loss of weight ($T_{10}$) was found. The relationship between degree of difunctional content and $T_{10}$ of the compounds tested is shown in FIG. 8, according to the test results. The results for ZTETRAOL 2000s (Comparative Example 1) which was the raw material of Compounds 1 and 2 and D-4OH (Comparative Example 2) which was the raw material of Compounds 3 to 6 are also shown for comparison.

In terms of the $T_{10}$ of Compounds 1 and 2 and Compounds 3 to 6, they had higher heat resistance than the raw materials ZTETRAOL 2000s and D-4OH. For the compounds which had been synthesized, the value of $T_{10}$ tended to rise as the degree of difunctional content increased. In particular, a $T_{10}$ value of at least 300° C. was obtained with the compounds where D-4OH was used as the raw material when the degree of difunctional content was about 15% or above. For the compounds where ZTETRAOL 2000s had been used as the raw material, when the degree of difunctional content was about 40% or above, a $T_{10}$ value of at least 300° C. was also obtained. Therefore, it is clear that the lubricants described herein according to various embodiments and approaches have a high heat resistance.

In one experiment, magnetic discs on which lubricating films comprising Compounds 1 and 2 synthesized as described previously were prepared and corrosion resistance tests were carried out. The corrosion test involved leaving discs on which each type of lubricating film had been formed with a thickness of about 1.0 nm to stand for 72 hours under conditions of a temperature of about 65° C. and a relative humidity of about 95%. Then, 3 ml of a mixed solution of 3% nitric acid and 3% hydrogen peroxide was dripped onto the disc surface and this stood for 1 hour at room temperature (25° C.). Then, the solution was recovered and the cobalt (Co) concentration was measured with high frequency induction coupled plasma mass spectroscopy (ICP-MS). The magnetic discs which had a laminated structure used in this example are described below.

A glass substrate of diameter 63.5 mm was washed and then a seed film, an undercoat film, a lower magnetic film, a nonmagnetic intermediate film, an upper magnetic film, and an amorphous carbon film were formed using a flat-leaf type sputtering apparatus. The seed film was sputtered using a NiTa alloy target and the film thickness was 30 nm. The thickness of the seed film was obtained by measurement with the fluorescence X-ray measuring method. After forming the seed layer, it was heated to 260° C. and exposed for 3.5 seconds in an Ar—$O_2$ mixed gas atmosphere. Then, a 5 nm CrTi alloy undercoat film was formed on the seed film and a 3.5 nm CoCrPt alloy magnetic film was formed as the lower magnetic layer, a 0.5 nm Ru film was formed as the intermediate film, and a 15 nm CoCrPtB alloy film was formed as the upper magnetic film. A 3.0 nm nitrogen-added carbon protective film was formed over the upper magnetic layer. The protective film may be a DLC film formed with a chemical vapor deposition (CVD) method or an ion beam deposition (IBD) method, or any other method as would be understood by one of skill in the art. The film thickness of the protective layer was determined using the X-ray reflection method by forming a 5 nm Cr film over the protective film in order to improve the accuracy of the film thickness measurement.

Discs formed as far as the protective film described herein were each provided with a lubricating film of about 1.0 nm by coating with a dip-coating method in a lubricant solution where Compound 1 or 2 has been dissolved in a suitable amount, e.g., in a 4:1 (by volume) mixed solvent of AK225 and acetone. The thickness of the lubricating films was measured with FT-IR. Magnetic discs were prepared this way. The results obtained on evaluating corrosion resistance are shown in Table 2, below. The results obtained with discs on which lubricating films which had the same perfluoropolyether chain and which only had the terminal structures changed (Comparative Examples 3 to 6) are also shown for comparison.

TABLE 2

| | Co Ion Concentration (µg/l) |
|---|---|
| Compound 1 | 8.5 |
| Compound 2 | 5.1 |
| Comparative Example 3 | 67.4 |
| Comparative Example 4 | 150.3 |
| Comparative Example 5 | 82.0 |
| Comparative Example 6 | 67.7 |

According to this table, the corrosion resistance with respect to Co differs according to the structure of the terminal functional groups, and the Co ion concentration with Compounds 1 and 2 was less than about one eighth (⅛) when compared with that of Comparative Example 3 which exhibited the lowest concentration among the lubricating films. The value here was a low concentration of less than 10 µg/l. Furthermore, on comparing Compounds 1 and 2 and Comparative Example 3 which was the raw material of these compounds, the Co ion concentration tended to fall as the degree of difunctional content increased.

It is thought that the high Co ion concentration in the case of Comparative Example 4 arose because the lubricant had undergone hydrolysis under the conditions of high temperature and humidity and the disc had become liable to corrosion. This conjecture is not meant to be limiting on any actual process that may have occurred. These results confirmed that the magnetic discs on which the perfluoropolyethers described herein had been formed as lubricating films had a high corrosion resistance in respect of Co, and the like.

In another experiment, magnetic discs on which Compounds 3 to 6 were formed as lubricating films were produced and corrosion resistance tests were carried out similar to in the previous example.

The magnetic discs (patterned media) used according to this example are described below. A glass substrate having a diameter of 63.5 mm was washed and then a binding layer film, a soft magnetic layer, a seed layer, and an intermediate layer were formed sequentially on the substrate using a sputtering apparatus. The binding layer comprised 10 nm of $Ni_{63}Ta_{37}$ and the soft magnetic layer comprised 50 nm of $Co_{92}Ta_3Zr_5$ as a first soft magnetic layer, 0.8 nm of Ru as a non-magnetic layer, and 50 nm of $Co_{92}Ta_3Zr_5$ as a second soft magnetic layer. The seed layer comprised 2 nm of $Ta_{70}Cr_{30}$ as a first seed layer and 5 nm of $Ni_{92}W_8$ as a second seed layer. The intermediate layer comprised 16 nm of Ru. The recording layer was formed with a pattern comprising 16 nm (largest part) regions made of the magnetic layer material CoCrPt—$SiO_2$ which formed the protrusions and filled regions made of the nonmagnetic material $SiO_2$ which had been formed in the concavities. Moreover, a 2.0 nm carbon protective layer was formed over the recording layer using the CVD method. Solutions where a suitable amount of Compounds 3 to 6 synthesized as previously described had been dissolved in VERTREL XF were used individually as lubricant solutions. Discs formed as far as the protective film described above were each provided with a lubricating film of about 1.0 nm by coating with the dip-coating method in the respective lubricant solution. The thickness the lubricating films was measured with FT-IR. Magnetic discs were prepared in this way.

The results obtained on evaluating the corrosion resistance are shown in Table 3. The result obtained with a disc on which a lubricating film of D-4OH which is the raw material of this example (Comparative Example 7) is also shown for comparison.

TABLE 3

| | Co Ion Concentration (µg/l) |
|---|---|
| Compound 3 | 9.9 |
| Compound 4 | 28.0 |
| Compound 5 | 8.1 |
| Compound 6 | 8.7 |
| Comparative Example 7 | 72.2 |

Figure 9:
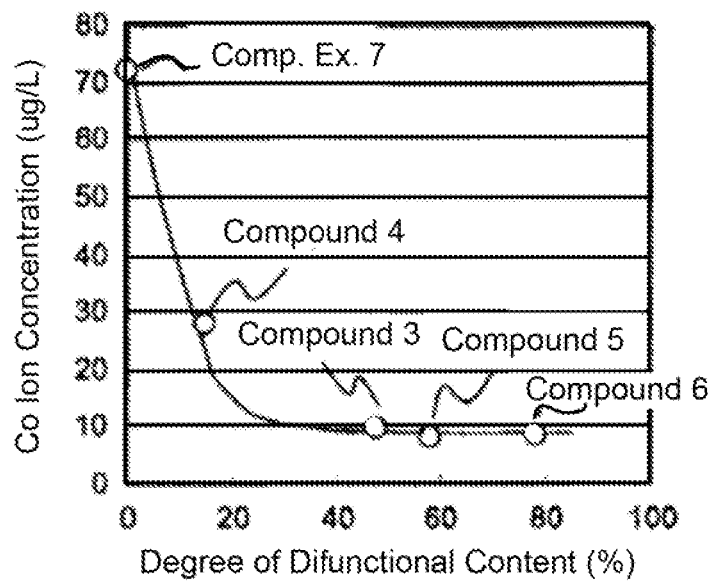
FIG. 9 is a chart depicting a relationship between the degree of difunctional content of a compound and the Co ion concentration, according to one embodiment.

Here, the molecular weight of the perfluoropolyether chain Rf(F) of the comparative example was 2055 and material from the lot used at the time of the synthesis was used. The relationship between the degree of difunctional content of a compound and the Co ion concentration is shown in FIG. 9, according to one embodiment.

According to this table, the corrosion resistance with respect to Co was such that the Co ion concentration was low when compared with the raw material D-4OH (Comparative Example 7) and it was confirmed that the magnetic discs on which perfluoropolyethers as described herein had been formed as lubricating films had a high corrosion inhibiting effect with respect to Co, and the like. Furthermore, the Co ion concentration tended to fall as the degree of difunctional content increased. According to FIG. 9, a degree of difunctional content of at least 25% (at least one of the terminal functional groups being represented by Group I) is preferred for improving the corrosion resistance since the Co ion concentration was of the order of about 10 µg/l when the degree of difunctional content of the compound was at least 25%.

In another example, the magnetic discs produced in this example were fitted onto a spin stand of the pin-on-disc type and, after housing this in a pulse-laser irradiating apparatus, an investigation of the heat resisting effect of the lubricating films was carried out by irradiating with the pulsed laser is such a way that the disc surface reached 300° C. The pulse-laser apparatus was constructed from a pulse laser body and radiation box, and a control unit, and inside the radiation box were housed a radiating probe which was connected to an optical fiber from the pulse laser body and an X—Y—Z stage over which the radiating probe moved, and the laser could be radiated onto any optional location on the disc surface. The spin-stand mentioned above was housed in the radiation box and pulse-laser irradiation was carried out shifting by 2.5 mm (radiation width 5 mm) to the left and right of a center at a radius of 21 mm on the disc as it was being rotated at 5400 rpm. Furthermore, the magnetic head swept the surface from a radius of 16 mm to a radius of 28 mm at the same time as the disc was being rotated. Moreover, the head load was 2 g and the head was in contact with the disc surface and the pulse laser continuously heated the disc surface in the vicinity of the magnetic head (on the flow-out end side).

Figure 10:
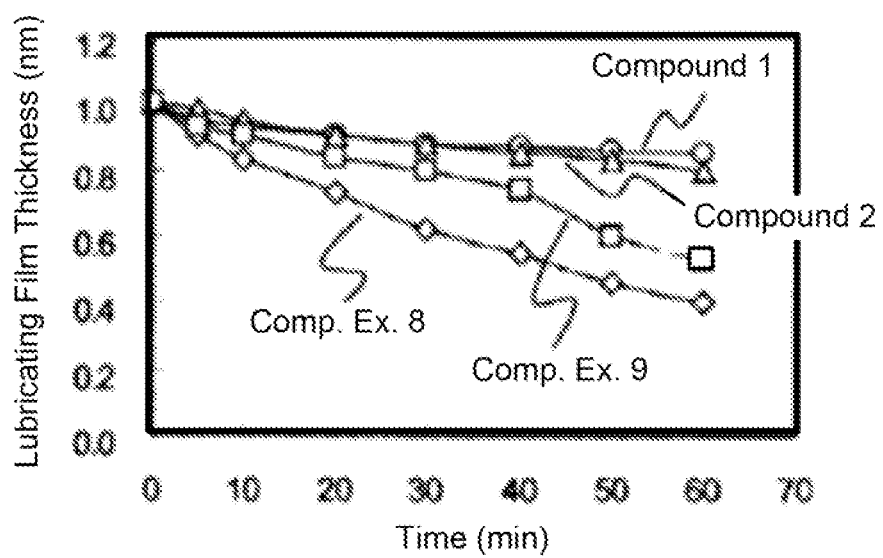
FIG. 10 is a chart depicting changes with respect to time in the lubricating layer thickness in the track parts which were heated with the pulse laser, according to one embodiment.

The changes with respect to time in the lubricating layer thickness in the track parts (radius 22 mm) which were heated with the pulse laser are shown in FIG. 10. The results obtained by carrying out the same evaluation with lubricating films (Comparative Examples 8 and 9) where the perfluoropolyether chain had the same structure and only the terminal structure was different are shown for comparison in Table 4. The bonding rate of each type of lubricating film is also shown in Table 4.

TABLE 4

|  | Bonding Rate (%) |
| --- | --- |
| Compound 1 | 53 |
| Compound 2 | 40 |
| Comparative Example 8 | 65 |
| Comparative Example 9 | 35 |

The lubricating films on the disc surface were constructed from a layer of lubricant which was strongly adsorbed on the disc surface (fixed layer) and a layer which was adsorbed weakly or not adsorbed at all (free layer). The bonding rate was determined by washing the lubricating film which had been formed with the solvent which was used during the formation of the lubricating layer, e.g., a mixed solvent comprising AK225 and acetone in proportions (by volume) of 4:1 in this example, measuring the film thickness again, and expressing this as a percentage with respect to the thickness of the lubricating film before washing. That is to say, bonding rate=fixed layer/initial film thickness, and this provides an index which indicates the strength of the adsorption on the protective film. The lubricating film thicknesses were measured with FT-IR. According to FIG. 10, the lubricating film thickness was reduced to 0.40 nm after 60 minutes from starting the measurement in the case (Comparative Example 8) where Z TETRAOL 2000s which is the raw material of this example was used for the lubricating film. Furthermore, although the reduction in the lubricating film thickness up to 40 minutes after starting measurement was small with Comparative Example 9 which had terminal benzotriazole linked with ether bonds, the thickness of the lubricating film fell suddenly after 40 minutes. On the other hand, as opposed to the results obtained with the comparative examples, stable heat resistance (and sliding durability) after 60 minutes was obtained with a lubricating film of about 0.85 nm with Compound 1 of this example and a lubricating film of about 0.8 nm with Compound 2. When compared with Compound 1 (degree of difunctional content 66%), the film thickness after the test with Compound 2 (degree of difunctional content 98%) had a slightly lower value than with Compound 1 in spite of the fact that it had a higher degree of difunctional content. The heat resistance ($T_{10}$) of compounds synthesized with Z TETRAOL 2000s as the raw material is such that $T_{10}$ tends to rise as the degree of difunctional content increases but it remains more or less constant at about 340° C. with degrees of difunctional content of 60% and above.

Furthermore, as shown in Table 1, on comparing the degrees of difunctional content of Compound 1 and Compound 2, that of Compound 1 is higher. This suggests that when the magnetic disc is being rotated while carrying out local heating at 200° C. and above, not only the heat resistance of the lubricant itself but the bonding rate of the lubricating film as well contributes to keeping the film reducing effect small. That is to say, not having all of R1 to R4 substituted with Group I but having at least one hydroxyl group (where R1 to R4 is represented by —H) in the molecule is more desirable for maintaining adhesion. It is thought that with Comparative Example 9, which had terminal benzotriazole, the bonding rate was low (Table 4) and the ether bonds were broken by heat, the benzotriazole groups were eliminated, and the terminal groups became —$CH_2OH$ and so the heat resistance could not be maintained after 40 minutes, with the result being that the thickness of the lubricating film was reduced.

In another example, heat resistance tests with local 300° C. overheating were carried out in the same way as in the previous example using magnetic discs which had been produced in the same way as in the previous example with Compounds 3 to 6 as lubricating films.

Figure 11:
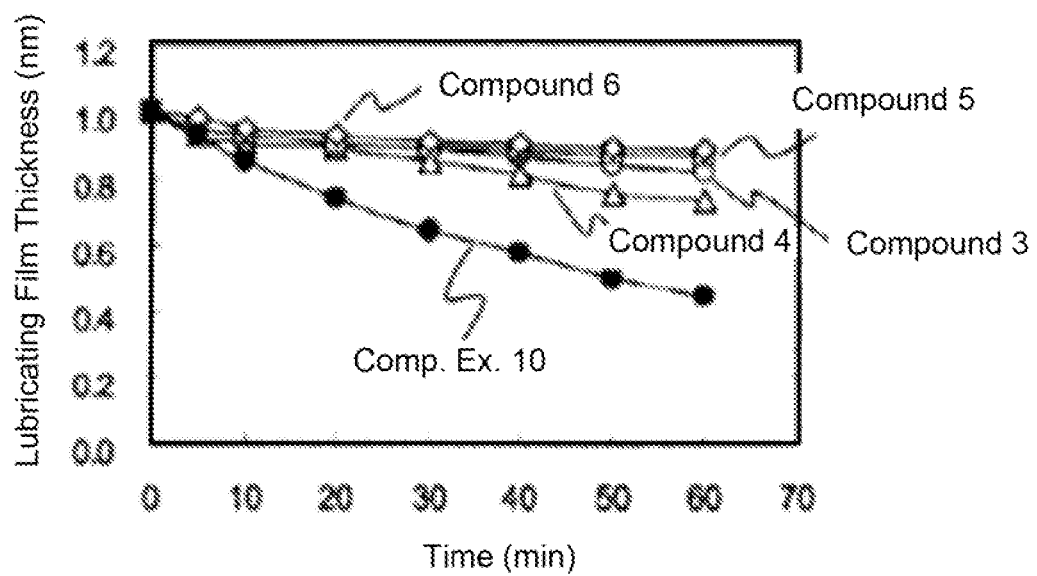
FIG. 11 is a chart depicting changes with respect to time in the lubricating layer thickness in the track parts which were heated with the pulse laser, according to one embodiment.

The changes with respect to time in the lubricating layer thickness of the track parts (radius 22 mm) which were heated with the pulse laser are shown in FIG. 11, according to one embodiment. The result obtained on carrying out the same evaluation using D-4OH which was the raw material of the compounds of this example for the lubricating film (Comparative Example 10) is also shown for comparison. The bonding rate of each type of lubricating film is shown in Table 5. Moreover, the lubricating films which had been formed were washed using VERTREL XF which is a solvent for calculating the bonding rate.

TABLE 5

|  | Bonding Rate (%) |
| --- | --- |
| Compound 3 | 59 |
| Compound 4 | 63 |
| Compound 5 | 57 |
| Compound 6 | 52 |
| Comparative Example 10 | 67 |

According to FIG. 11, the lubricating film thickness was reduced to 0.45 nm, less than half the initial film thickness, after 60 minutes from starting the measurement in the case (Comparative Example 10) where D-4OH which is the raw material of this example was used for the lubricating film. On the other hand, as opposed to the result obtained with the comparative example, when Compounds 3 to 6 of this example were used as lubricating films the lubricating films were thicker than about 0.70 nm after 60 minutes and heat resistance (and running durability) that was stable to local heating to more than 200° C. was obtained. Table 5 suggests that when the magnetic discs are rotated while carrying out local heating above 200° C. not only the heat resistance of the lubricant itself but the bonding rate of the lubricating film as well contributes to keeping the film reducing effect small. That is to say, a bonding rate of at least 25% is preferred, and a bonding rate of from 40% to 80% is especially desirable, in various embodiments, for maintaining a lubricating film which has both heat resistance and corrosion resistance.

In Comparative Example 1, the 10% weight loss temperature ($T_{10}$) was measured under the same conditions as in the first example using the lubricating agent ZTETRAOL 2000s (Mn of Rf(F) 1730) which is the raw material of Compounds 1 and 2. The result is also shown in FIG. 8.

In Comparative Example 2, the 10% weight loss temperature ($T_{10}$) was measured under the same conditions as in the first example using the lubricating agent D-4OH (Mn of Rf (D) 2055) which is the raw material of Compounds 3 to 6. The result is also shown in FIG. 8.

For Comparative Examples 3 to 6, the structures of the lubricating films used in Comparative Examples 3 to 6 and the average molecular weights (Mn) of the perfluoropolyether chain Rf(F) are shown in Table 6.

TABLE 6

| | Chemical Structure | Mn | Information |
|---|---|---|---|
| Comp. Ex. 3 | Rf(F)—(CH$_2$—O—CH$_2$—CH(OH)—CH$_2$OH)$_2$ | 1730 | ZTETRAOL 2000s produced by the Solvay Solexis company |
| Comp. Ex. 4 | Rf(F)—(COOR)$_2$ Where R is an alkyl group (a mixture of methyl and ethyl groups) | 2000 | Z DEAL produced by the Ausimont company |
| Comp. Ex. 5 | Rf(F)—(CH$_2$OH)$_2$ | 1980 | Z DOL2000s produced by the Solvay Solexis company |
| Comp. Ex. 6 | Rf(F)—(CH$_2$OH)$_2$ | 1980 | Z DOL2000s produced by the Solvay Solexis company |
| | 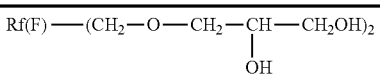 | 2020 | A2OH produced by the MORESCO company |

Here Rf(F) is —CF$_2$O(CF$_2$CF$_2$O)$_m$(CF$_2$O)$_n$CF$_2$— (where m and n represent 0 and/or a positive integer). The lubricants shown in Table 6 were used as lubricating films on magnetic discs which had the same film structure excluding the lubricating film as in the second example. Lubricating films of about 1.0 nm in each case were formed by coating with the dip-coating method in lubricant solutions where the Comparative Examples 3 to 6 shown in Table 6 had been dissolved in suitable amounts in VERTREL XF. The lubricating film thicknesses were measured with FT-IR. Magnetic discs were produced in this way. Corrosion resistance evaluations were carried out in the same way as in the second example and the results are also shown in Table 2.

In Comparative Example 7, a magnetic disc with a similar film structure excluding the lubricating film of the third example was used, using the lubricating agent D-4OH.

A lubricating film of about 1.0 nm was formed by coating with the dip-coating method in a lubricant solution where D-4OH had been dissolved in a suitable amount in VERTREL XF. The lubricating film thickness was measured with FT-IR. A magnetic disc was produced in this way. Corrosion resistance evaluation was carried out in the same way as in the third example and the result is also shown in Table 3 and FIG. 8.

In Comparative Examples 8 and 9, the structures of the lubricating films and the average molecular weights (Mn) of the perfluoropolyether chain Rf(F) are shown in Table 7.

TABLE 7

| | Chemical Structure | Mn | Information |
|---|---|---|---|
| Comp. Ex. 8 | Rf(F)—(CH$_2$—O—CH$_2$—CH(OH)—CH$_2$OH)$_2$ | 1730 | ZTETRAOL 2000s produced by the Solvay Solexis company |
| Comp. Ex. 9 | 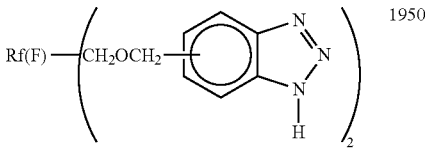 | 1950 | |

Here Rf(F) is —CF$_2$O(CF$_2$CF$_2$O)$_m$(CF$_2$O)$_n$CF$_2$— (where m and/or n represent 0 or a positive integer).

Using magnetic discs with a similar film structure excluding the lubricating film of the second example, the lubricants shown in Table 7 were used as lubricating films. Lubricating films of about 1.0 nm were formed by coating with the dip-coating method in lubricant solutions where Comparative Example 8 or 9 shown in Table 7 had been dissolved in a suitable amount in VERTREL XF. The lubricating film thicknesses were measured with FT-IR. Magnetic discs were produced in this way. Heat resistance tests with 300° C. local heating were carried out in a similar way as in the fourth example and the results are also shown in FIG. 10 and Table 4.

In Comparative Example 10, a lubricating film of 1.0 nm was formed on a magnetic disc which had the same film structure up to the film structure excluding the lubricating film of the second example using the lubricant used in Comparative Example 7. The lubricating film thickness was measured with FT-IR. A magnetic disc was produced in this way. A heat resistance test with 300° C. local heating was carried out in a similar way as in the fifth example and the result is also shown in FIG. 11 and Table 5.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A lubricant, comprising a perfluoropolyether having a chemical structure of:

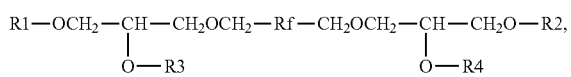

wherein Rf is at least one of: —CF$_2$O(CF$_2$CF$_2$O)$_m$(CF$_2$O)$_n$CF$_2$— and —CF$_2$CF$_2$O(CF$_2$CF$_2$CF$_2$O)$_k$CF$_2$CF$_2$—, with m representing 0 or a positive integer, n representing 0 or a positive integer, and k representing 0 or a positive integer, and wherein R1, R2, R3 and R4 are selected from a group consisting of —H or

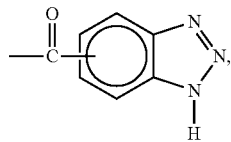

with at least one of R1, R2, R3 and R4 being

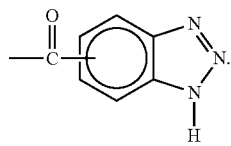

2. A magnetic recording medium, comprising:
a magnetic recording layer above a nonmagnetic substrate;
a protective film above the magnetic recording layer; and
a lubricant as recited in claim 1 positioned above the protective film.

3. A magnetic data storage system, comprising:
at least one magnetic head;
the magnetic recording medium as recited in claim 2;
a drive mechanism for passing the magnetic recording medium over the at least one magnetic head; and
a controller electrically coupled to the at least one magnetic head for controlling operation of the at least one magnetic head.

4. A magnetic recording medium, comprising:
a magnetic recording layer above a nonmagnetic substrate, the magnetic recording layer comprising concavities and protrusions on an upper surface thereof, wherein the protrusions of the magnetic recording layer are magnetic regions and the concavities of the magnetic recording layer are nonmagnetic regions; and
a lubricant as recited in claim 1 positioned above the magnetic recording layer.

5. The magnetic recording medium as recited in claim 4, further comprising a protective film positioned above the magnetic recording layer and below the lubricant.

6. A magnetic data storage system, comprising:
at least one magnetic head;
the magnetic recording medium as recited in claim 5;
a drive mechanism for passing the magnetic recording medium over the at least one magnetic head; and
a controller electrically coupled to the at least one magnetic head for controlling operation of the at least one magnetic head.

7. The lubricant as recited in claim 1, characterized in that an average molecular weight of the lubricant is from about 1,500 to about 4,500 and a molecular weight distribution of the lubricant is not more than about 1.5.

8. A lubricant, comprising a perfluoropolyether having a chemical structure of:

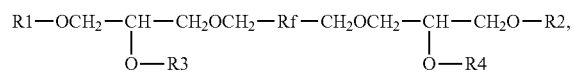

wherein Rf comprises: —CF$_2$O(CF$_2$CF$_2$O)$_m$(CF$_2$O)$_n$CF$_2$—, with m representing 0 or a positive integer, n representing 0 or a positive integer, and wherein R1, R2, R3 and R4 are selected from a group consisting of —H or

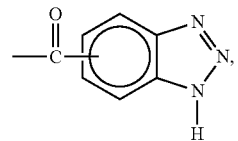

with at least one of R1, R2, R3 and R4 being

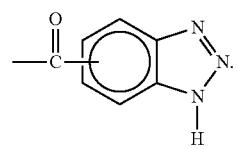

9. The lubricant as recited in claim 8, characterized in that an average molecular weight of the lubricant is from about 1,500 to about 4,500 and a molecular weight distribution of the lubricant is not more than about 1.5.

10. A magnetic recording medium, comprising:
a magnetic recording layer above a nonmagnetic substrate;
a protective film above the magnetic recording layer; and
a lubricant as recited in claim 9 positioned above the protective film.

11. A magnetic data storage system, comprising:
at least one magnetic head;
the magnetic recording medium as recited in claim 10;
a drive mechanism for passing the magnetic recording medium over the at least one magnetic head; and
a controller electrically coupled to the at least one magnetic head for controlling operation of the at least one magnetic head.

12. A magnetic recording medium, comprising:
a magnetic recording layer above a nonmagnetic substrate, the magnetic recording layer comprising concavities and protrusions on an upper surface thereof, wherein the protrusions of the magnetic recording layer are magnetic regions and the concavities of the magnetic recording layer are nonmagnetic regions; and a lubricant as recited in claim 9 positioned above the magnetic recording layer.

13. The magnetic recording medium as recited in claim 12, further comprising a protective film positioned above the magnetic recording layer and below the lubricant.

14. A magnetic data storage system, comprising:

at least one magnetic head;

the magnetic recording medium as recited in claim 13;

a drive mechanism for passing the magnetic recording medium over the at least one magnetic head; and a controller electrically coupled to the at least one magnetic head for controlling operation of the at least one magnetic head.

15. A lubricant, comprising a perfluoropolyether having a chemical structure of:

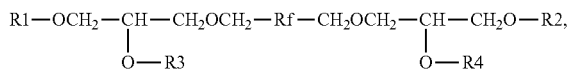

wherein Rf comprises: $-CF_2CF_2O(CF_2CF_2CF_2O)_kCF_2CF_2-$, with k representing 0 or a positive integer, wherein R1 to R4 are selected from a group consisting of —H or

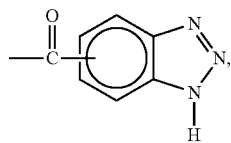

with at least one of R1, R2, R3 and R4 being

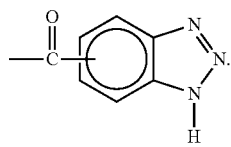

16. The lubricant as recited in claim 15, characterized in that an average molecular weight of the lubricant is from about 1,500 to about 4,500 and a molecular weight distribution of the lubricant is not more than about 1.5.

17. A magnetic recording medium, comprising:

a magnetic recording layer above a nonmagnetic substrate;

a protective film above the magnetic recording layer; and a lubricant as recited in claim 15 positioned above the protective film.

18. A magnetic data storage system, comprising:

at least one magnetic head;

the magnetic recording medium as recited in claim 17;

a drive mechanism for passing the magnetic recording medium over the at least one magnetic head; and a controller electrically coupled to the at least one magnetic head for controlling operation of the at least one magnetic head.

19. A magnetic recording medium, comprising:

a magnetic recording layer above a nonmagnetic substrate, the magnetic recording layer comprising concavities and protrusions on an upper surface thereof, wherein the protrusions of the magnetic recording layer are magnetic regions and the concavities of the magnetic recording layer are nonmagnetic regions;

a protective film positioned above the magnetic recording layer and below the lubricant; and a lubricant as recited in claim 15 positioned above the protective film.

20. A magnetic data storage system, comprising:

at least one magnetic head;

the magnetic recording medium as recited in claim 19;

a drive mechanism for passing the magnetic recording medium over the at least one magnetic head; and a controller electrically coupled to the at least one magnetic head for controlling operation of the at least one magnetic head.

* * * * *

UNITED STATES PATENT AND TRADEMARK OFFICE
CERTIFICATE OF CORRECTION

| | | |
|---|---|---|
| PATENT NO. | : 8,628,869 B2 | Page 1 of 1 |
| APPLICATION NO. | : 13/361896 | |
| DATED | : January 14, 2014 | |
| INVENTOR(S) | : Amo et al. | |

It is certified that error appears in the above-identified patent and that said Letters Patent is hereby corrected as shown below:

In the specification:

col. 11, line 36 replace "FIFE" with --HFE--;

col. 15, line 10 replace "Was" with --was--;

col. 15, line 26 replace "carboxylmide" with --carboxyimide--.

Signed and Sealed this
Twenty-ninth Day of April, 2014

Michelle K. Lee
*Deputy Director of the United States Patent and Trademark Office*